United States Patent [19]

Paret et al.

[11] Patent Number: 5,536,864
[45] Date of Patent: Jul. 16, 1996

[54] PROCESS FOR PRODUCING DIMETHYL CARBONATE AND APPARATUS SUITABLE FOR SUCH PURPOSE

[75] Inventors: Giancarlo Paret, San Donato Milanese; Gianni Donati, Rho; Maurizio Ghirardini, Milan, all of Italy

[73] Assignee: Enichem Synthesis S.p.A., Palermo, Italy

[21] Appl. No.: 364,520

[22] Filed: Dec. 27, 1994

Related U.S. Application Data

[63] Continuation of Ser. No. 240,968, May 10, 1994, abandoned, which is a continuation of Ser. No. 709,584, Jun. 3, 1991, abandoned.

[30] Foreign Application Priority Data

Jun. 4, 1990 [IT] Italy ................................. 20531 A/90

[51] Int. Cl.$^6$ ..................................................... C07C 69/96
[52] U.S. Cl. ............................................................ 558/277
[58] Field of Search ............................ 558/277; 422/211, 422/231

[56] References Cited

U.S. PATENT DOCUMENTS

| | | | |
|---|---|---|---|
| 3,487,621 | 1/1970 | Bichet | 55/228 |
| 3,882,167 | 5/1975 | Lohmar et al. | 560/205 |
| 4,218,391 | 8/1980 | Ramano | 558/277 |

FOREIGN PATENT DOCUMENTS 0366177  5/1990  European Pat. Off. .

*Primary Examiner*—Gary Geist
*Assistant Examiner*—Joseph M. Conrad, III
*Attorney, Agent, or Firm*—Rogers & Wells

[57] ABSTRACT

The reaction between methanol, carbon monoxide and oxygen for preparing dimethyl carbonate, in the presence of cuprous chloride as the catalyst, is carried out in a special reactor constituted by two parallel, vertical tubes, at the base of one of which the fresh gas and the recycle gas are fed; the reaction products are separated by partially condensing the recirculate vapors.

20 Claims, 4 Drawing Sheets

PROCESS FOR PRODUCING DIMETHYL CARBONATE AND APPARATUS SUITABLE FOR SUCH PURPOSE

This is a continuation of application Ser. No. 08/240,968, filed May 10, 1994, now abandoned, which is a continuation of Ser. No. 07/709,584, filed Jun. 3, 1991, now abandoned, entitled PROCESS FOR PRODUCING DIMETHYL CARBONATE AND APPARATUS SUITABLE FOR SUCH PURPOSE.

The present invention relates to an improved process for producing dimethyl carbonate (referred to as DMC in the following) by starting from CO, $O_2$ and methanol, in the presence of CuCl as the catalyst, a process according to which the reaction is carried out in a heterogeneous-phase system containing substances in the gas, liquid and solid phases, in a special reactor constituted by two parallel, vertical tubes, at the base of one of which the fresh gas and the recycle gas are fed, so as to obtain a recirculation of the liquid phase due to the difference in density which is generated between the upwards tube, containing the gas, and the downward tube, in which a lower amount of gas is contained.

The esters of carbonic acid are known, which find use as solvents and as agents of polymerization by transesterification of glycols and bis-phenols in the production of polycarbonates.

It is known as well that the most common methods for preparing such compounds have been based for long time on the reaction between an alcohol and phosgene or chloroformates, carried out in the presence of suitably selected bases, methods by now blamed from many viewpoints, due to the inherent riskfulness of the system.

Processes for preparing esters of carbonic acid are known as well, which do not use phosgene, but which, however, not always lead to satisfactory results when the relevant technology is transferred to the commercial level.

For example, Japanese Patent No. 11,129 discloses the preparation of carbonate esters by reaction of an alcohol with carbon monoxide in the presence of cupric ions: the yields of carbonate are extremely low and furthermore, as the reduction proceeds, considerable amounts are formed of alkyl halide, ether and halogen-containing acid, with an increased acidification of the system being caused.

The same Applicant controls a large number of patents relevant to the oxidative carbonylation of alcohols with carbon monoxide and oxygen: for example, Italian Patent No. 898,077, relating to a process for preparing esters of carbonic acids, which consists of the reaction between an alcohol, carbon monoxide and oxygen, carried out in the presence of a catalytic system consisting of complexes of metals capable of existing in two different valency states; or Italian Patent No. 1,070,574, which discloses a preparation of carbonic acid esters by means of the reaction of an alcohol with oxygen and carbon monoxide in the presence of a catalyst preferably constituted by a salt of cuprous copper; or Italian Patent No. 1,127,270 which, by referring to the reaction as per the prior Patent, discloses the feasibility thereof by starting from a gas mixture constituted by hydrogen, carbon monoxide and oxygen.

The presently most widely used route is based on the use of a catalyst consisting of cuprous chloride and is essentially based on the following reaction $$2CH_3OH+CO+\tfrac{1}{2}O_2 \rightarrow (CH_3O)_2CO+H_2O$$

The reaction proceeds through the two steps of oxidation and reduction: without wishing to enter in detail into the actual mechanism of reaction, the Applicant thinks that in the first step cuprous chloride reacts with methanol and oxygen to form a cupric methoxy chloride which, in the second step, would be reduced by carbon monoxide, with dimethyl carbonate being produced and cuprous chloride being regenerated:

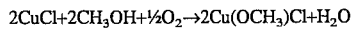

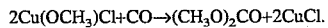

The oxidative carboxylation is carried out in the liquid phase through two reactors, with the effluents from the bottom of the first reactor being fed to the top of the second reactor.

The present Applicant has found now an operating solution which makes it possible to carry out the above process with a particularly simple separation of the liquid reaction products from the catalyst, without the latter having to be removed from the reactor.

BRIEF DESCRIPTION OF THE DRAWINGS

FIGS. 1 and 4 show the above mentioned reactor while

Such a solution, which is the subject-matter of the present invention, is based on the reaction for preparing dimethyl carbonate from CO, $O_2$ and methanol being carried out in a reactor essentially comprising two parallel, vertical tubes, connected with each other at their top ends and at their bottom ends, at the base of one of which the fresh gas and the recycle gas are fed, so that a recirculation and consequent mixing of the liquid is obtained, thanks to the difference in density which is generated between the upwards tube, which contains the gas and the downwards tube which contains a smaller amount of gas.

Under the operating conditions, the recycle gas is saturated with the vapours coming from the reaction liquid; methanol is the most volatile component, followed by DMC and water; inasmuch as the reaction produces one water molecule per each DMC molecule, the removal of water from the reaction system is the controlling parameter in order to keep steady-state reaction conditions, i.e., a constant-composition reaction liquid.

By partially condensing the vapours contained in the recycle gas, a liquid is obtained, whose composition is close to the composition of the reaction liquid. From said liquid, water to be discharged, produced DMC and a stream of methanol to be recycled to the reaction together with an aliquot of DMC --which normally is extracted in excess over water --as it will result more clearly from the following examples, are then separated by means of techniques known.

The proposed solution can be implemented of course according to other operating solutions with respect to the configuration of reactors which, meeting the principles described hereinabove, must be regarded as fully equivalent to the reactor disclosed in the following and therefore falling within the scope of the present invention.

Figure 1A:
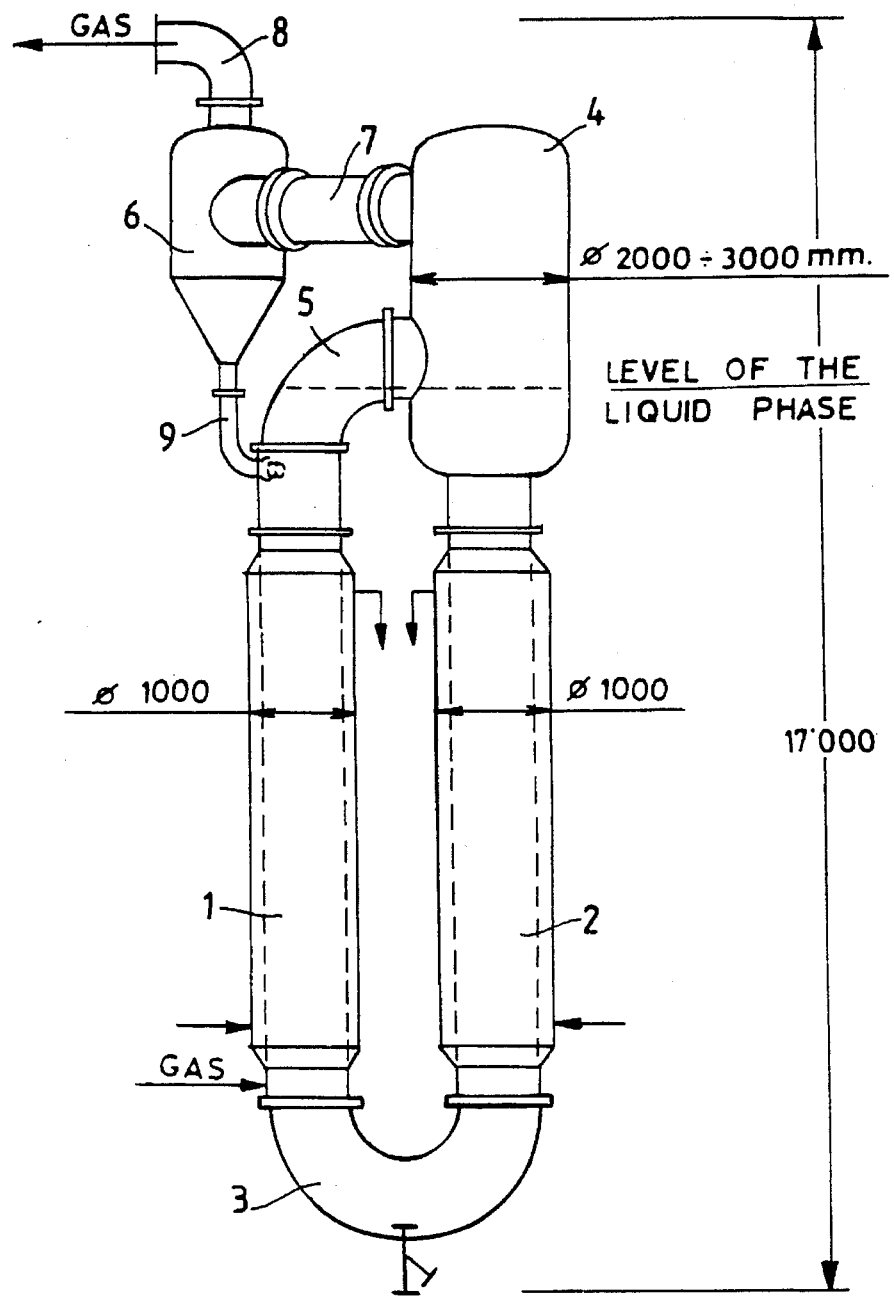
Figure 1B:
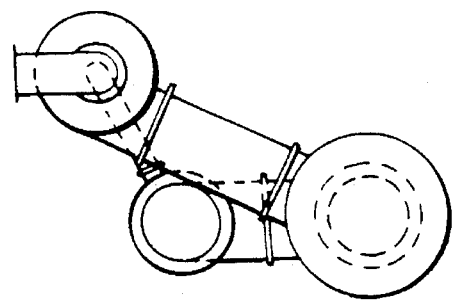

The reactor for practicing the process according to the present invention is constituted by two tubes provided with an inner enamel lining and an outer jacket (1 and 2 in FIG. 1).

The gas is fed to the bottom of one of said tubes by means of a suitable gas distributor.

At their bottom end, the tubes are smoothly connected with each other by a bent pipe portion (3) provided with an inner enamel lining; at their top end, they are both connected with the vessel (4) also provided with an internal enamel lining, and namely, the tube (1) by means of the 90°-bent fitting (5), and the tube (2) directly through a hole provided at the bottom end of the vessel (4). Vessel (4) is connected to a separating cyclone (6) through a straight fitting (7). The separating cyclone (6) has a gas outlet (8) at its upper end and a fluid outlet (9) at its bottom end. The fluid outlet (9) is introduced into the lower part of the 90°-bent fitting (5) below the level of the liquid in the bent fitting (5).

When the process is started, the liquid with the catalyst is charged to the tubes, until it comes to lap the bottom portion of the bent pipe (5), and the gas feed is then started; said gas feed causes the liquid to be recirculated, with the circulation flowrate of the liquid being higher, as the volume flowrate of the gas.

For the tubes (1) and (2), diameters comprised within the range of from 0.025 to 1 m are adopted, with their length being comprised within the range of from 1.5 to 20 meters; the vessel (4) as a diameter which is from 2 to 4 times as large as the diameter of the tubes (1) and (2), and a height of from 2 to 10 times as large as the diameter.

The diameter of (4) must be larger than the diameter of tubes (1) and (2), so as to enable the separation between the gas and the liquid to occur.

The operating conditions are as follows: the operating temperatures are comprised within the range of from 80° C. to 200° C., and preferably of from 100° C. to 180° C.

The pressure is comprised within the range of from 10 to 50 bar.

The gas flowrate per each unit of surface area of the cross-section of the tubes is comprised within the range of from 100 to 1000 $m^3/m^2$.

Figure 2:
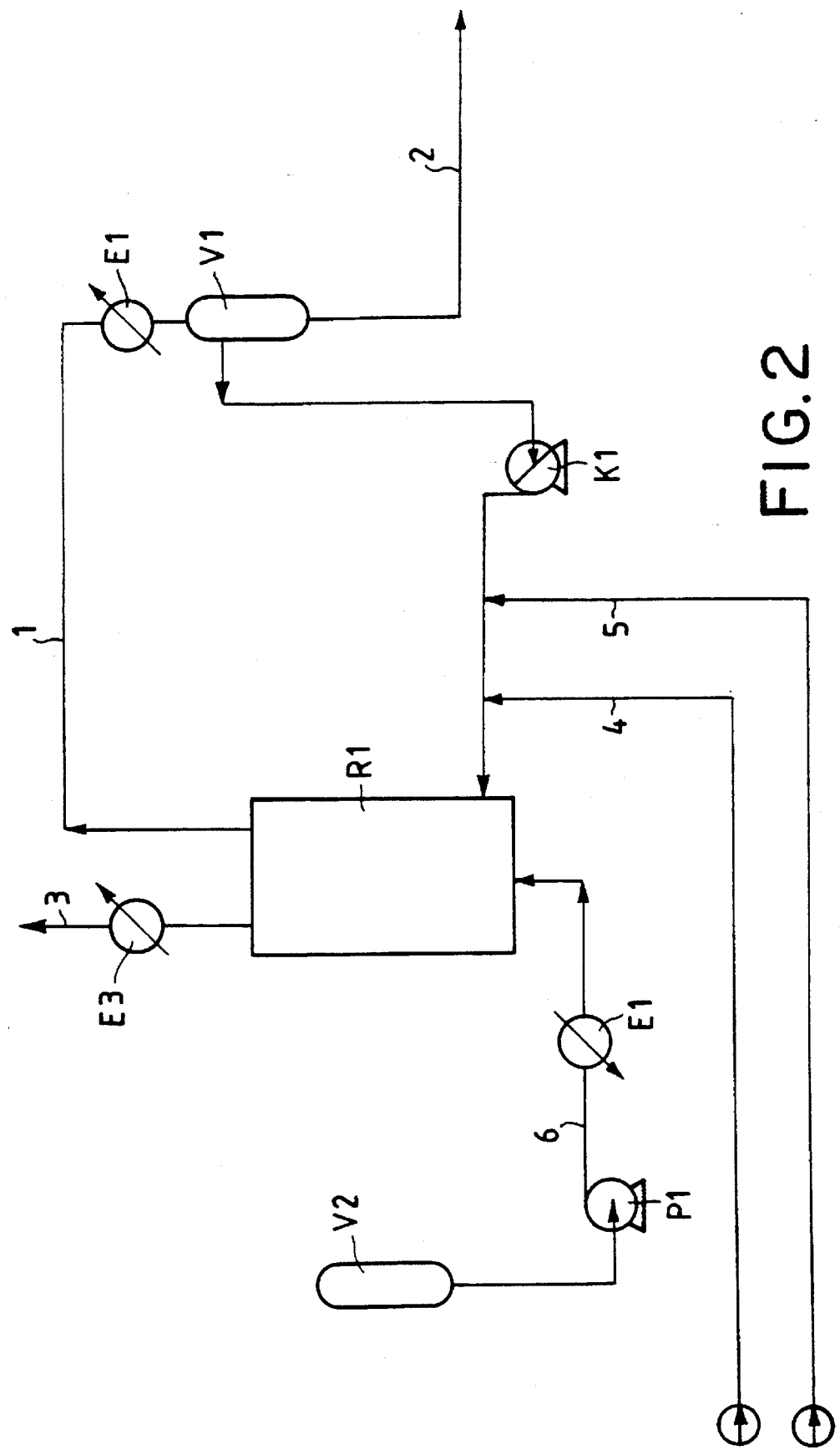
FIGS. 2 and 3 show the preparation cycle for the dimethylcarbonate.

In FIG. 2 a possible operating cycle is reported, still for exemplifying purposes, which makes it possible to carry out an operating cycle which enables the process for preparing dimethyl carbonate according to the principles of the present invention to be practiced.

In order to operate correctly, the reactor disclosed requires a high gas flowrate, which gas reacts to only a low percentage per each pass, with the unreacted portion being recycled to the bottom end of the reactor.

The recycle gas may have a very variable composition, also as a function of the operating conditions adopted; it is preferable to operate with an excess of CO and a less-than-stoichiometric amount of oxygen, so as to remain outside the concentration limit of the explosive mixtures.

The composition of the gas may vary within the range of from 99% CO to 25% CO, oxygen within the range of from 1 to 15%, with the balance to 100 being $N_2$, Ar, $CH_4$, $H_2$ and $CO_2$ or other gases which are inert in the reaction system.

During the reaction, oxygen and CO are consumed in the stoichiometric ratio of 1:2 by mol.

Inasmuch as also $CO_2$ is produced, some gas should be vented off from the system, also if pure gases are fed; the best point for this vent (3) is at the top end of the reactor, with a reflux condenser being provided, in order that the vapours are condensed and the escape of products or reaction solvent is prevented.

The composition of the reaction solvent may be very variable; it may range from nearly pure methanol, up to mixtures containing up to 10–25% of water by weight and/or up to 50–60% of DMC by weight, with the balance to 100% being methanol.

To this liquid, an amount of CuCl is added, which is comprised within the range of from 1% by weight to 20% by weight.

The reaction temperature is comprised within the range of from 80° C. to 200° C., and the operating pressure is comprised within the range of from 10 bar to 50 bar.

The recycle gas leaves the reactor saturated with vapours at the operating temperature.

The level of vapours in the gas may vary with the composition of the reaction liquid, the total pressure and temperature; in any case, it will be a significant percentage of the recirculated gas phase.

By means of a cooling of a few degrees (of from 3° to 30° C.), a partial condensation can be accomplished; the condensate liquid is richer in water and DMC than the vapour phase, with a composition similar to the composition of the reaction liquid (from 10 to 70% of vapours present).

This liquid phase should be kept circulating with a flowrate at which water and DMC produced by the reaction leave the reactor; in case an excess is drawn, the reaction liquid will be depleted of water and DMC and will be enriched with methanol; in case a too small amount is drawn, the liquid, and hence the equilibrium vapour, will be enriched with water and DMC.

Therefore, the system is capable of self-regulating within the limits of the kinetics of the formation of DMC.

After the separation of the condensate liquid, the gas is compressed back to the reaction pressure, by the compressor K1, and is fed back to the reactor.

To the gas recycle stream, fresh oxygen and CO are added, streams (4) and (5), in amounts equivalent to the amounts which react, plus the amount leaving the system, as said, with the stream (3).

Downstream of the compressor, to the reactor methanol is fed in an amount which corresponds to the methanol amount which will react, plus the methanol amount extracted in excess by means of stream (2), and the possible excess of DMC removed (stream (6)).

The addition of liquid should be such as to keep constant the liquid level inside the reactor, with the volume changes of the reaction medium being compensated for.

Further details of the process according to the present invention will be clear from the reading of the following examples: in such examples, obviously reported for merely illustrative purposes, only the reactor was used, the description of which is reported in the following.

The reactor is totally constituted by enamel-coated steel, to prevent corrosions.

The reactor is constituted by two tubes of 25 mm of inner diameter, provided with an internal enamel lining and an external jacket; both tubes are connected with each other at their bottom and top ends.

In the top portion of the reactor, a tube of 75 mm of diameter is installed; thanks to the decrease in velocity, the gas is separated from the recirculated liquid.

Figure 4:
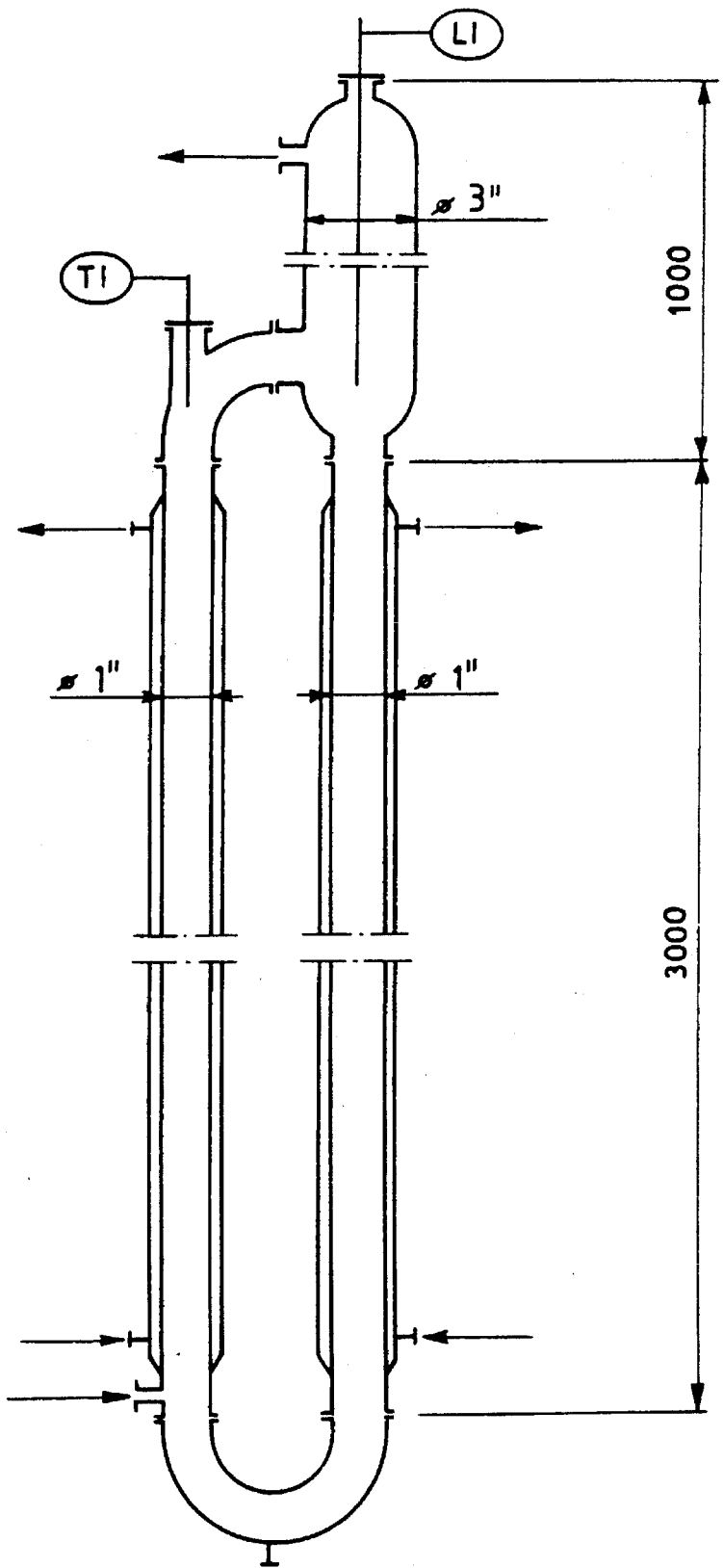

The gas is fed to the bottom portion of the reactor through a pipe (FIG. 4). The available volume for the liquid phase is of approximately 5 liters.

Figure 3:
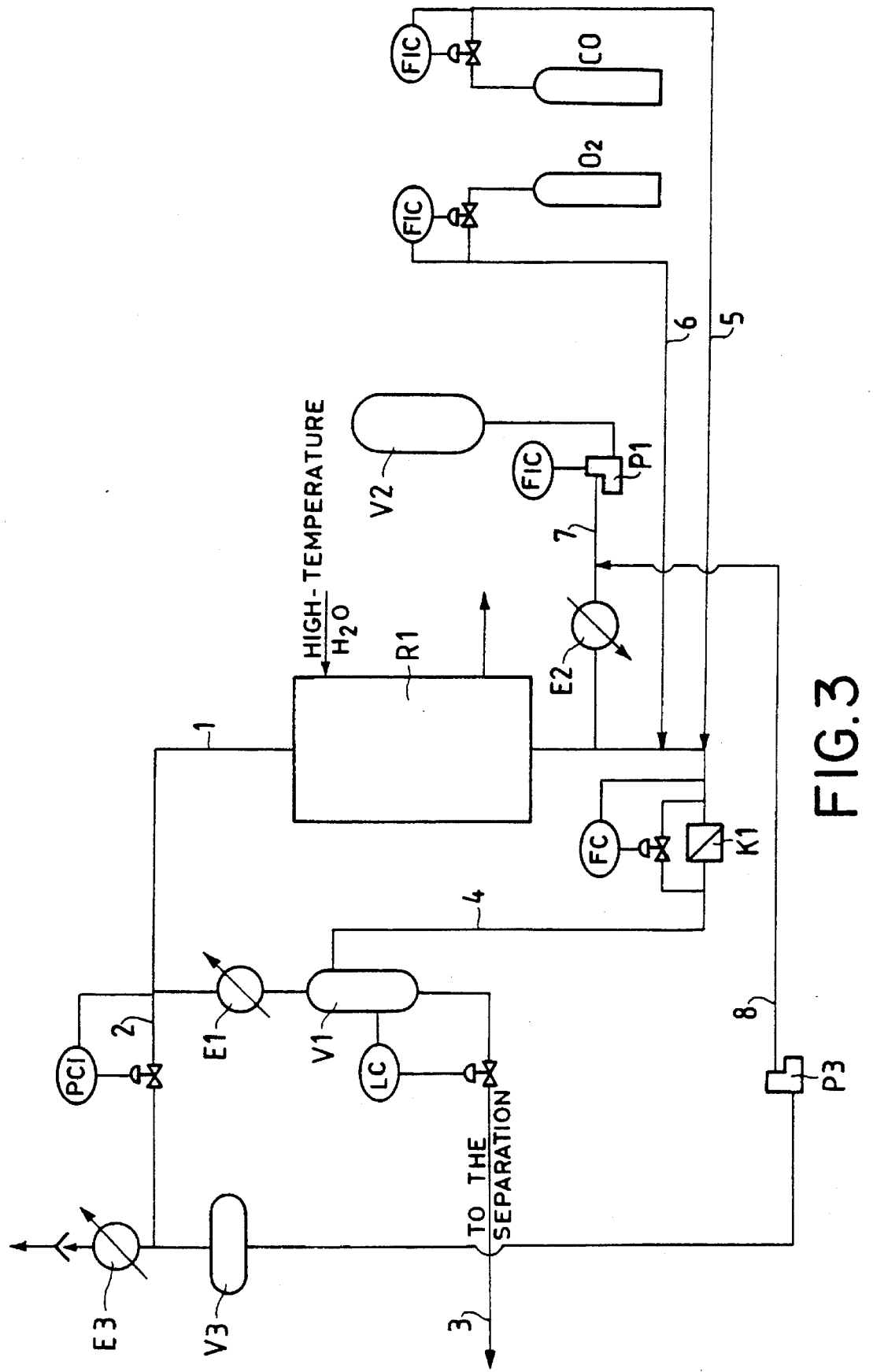

The flow scheme of the process is shown in FIG. 3.

The gas stream leaving the reactor (1) goes to the condenser E1, in which a portion of vapours is condensed; the condensate liquid (3) containing water, DMC and methanol under level control, goes to the separation.

The gas, containing the non-condensed vapours (4) goes to the compressor K1 which feeds it to the bottom portion of the reactor.

Carbon monoxide and oxygen fed as raw materials to the reactor are supplied from cylinders under flowrate control, to the main gas stream (5 and 6).

Methanol and DMC contained in V2 are fed (7) to the reactor by the pump P1, through the heat exchanger E2, with the necessary enthalpy level in order not to have to supply or remove heat to/from the reactor.

The vapours contained in the discharged overhead stream (2) are condensed in E3, collected in V3 and, through the pump P3, they are back sent to the reactor together with the stream (7) (owing to problems of overall dimensions, a reflux condenser was not used).

EXAMPLE NO. 1

The process was carried out at 30 bar and at 150° C.

A total volume of 5000 cc of a liquid having the molar composition

| *Methanol | 60% |
|---|---|
| *DMC | 25% |
| *Water | 15% | was charged to the reactor.

0.5 kg of CuCl was added.

The system was heated up to the required operating temperature (150° C.) and the reactor was pressurized with CO (30 bar), with the pressure control on the gas loop (9) being enabled, and the compressor K1 was started up, with a recycle flowrate of 250 l/h.

The feed of CO was started up at the required flowrate of 10.5 gram-moles/h (5), with the necessary amount for maintaining a constant pressure being discharged through the line 2.

As soon as the feed of oxygen (6) was started up, the reaction began, and the flowrate was adjusted to the planned value of 2.5 mol/h within approximately 1 hour.

The condensation of the product was started with a temperature change of 6° C. between the line upstream and the line downstream of the condenser E1.

As soon as inside the collection vessel the liquid reached the desired level, the condensate from the gas vent (8) was fed to the reactor.

Simultaneously, the feed of azeotropic mixture MeOH/DMC and fresh methanol (7) was started, so as to keep constant the liquid level inside reactor R1.

After approximately 1 hour, the system had reached its steady-state operating conditions, with the flowrate shown in the following, reported in weight units.

The run was continued for about four hours, and 1000 g of DMC was produced.

At the end of the test, the composition of the liquid resulted to be substantially the same as of the charged liquid.

EXAMPLE NO. 2

The process was carried out at 20 bar and at 120° C.

A total volume of 5000 cc of a liquid having the molar composition

| *Methanol | 70% |
|---|---|
| *DMC | 20% |
| *Water | 10% | was charged to the reactor.

250 g of CuCl was added.

The reaction was started by the same procedure as of Example 1.

The process was carried out with a flowrate of recycle gas of 200 l/h at 20 bar and 120° C., with 50% of vapours contained in the recycle stream being condensed.

During the test time of 6 hours under steady-state conditions a production rate of 135 g/h of DMC was obtained, which corresponds to 800 g.

EXAMPLE NO. 3

The test run was carried out at 25 bar and 130° C. To the reactor a total volume of 5000 cc was charged of a mixture having the molar composition

| *Methanol | 70% |
|---|---|
| *DMC | 20% |
| *Water | 10% | to which 1000 g of CuCl was added.

A stream of CO of 80%, with the balance to 100% being hydrogen, was fed, still from a cylinder (a cylinder charged with the mixture was used).

The same start up procedure of Example 1 was used, with a recycle flowrate of 380 l/h being maintained by the compressor K1, and the CO-$H_2$ mixture was fed at the flowrate of 16.25 mol/h (5), with the pressure inside the system being maintained by means of the pressure control and the vent 2.

As soon as the feed of oxygen was started up, the reaction began, and the flowrate of oxygen supply was adjusted to the planned value of 1.7 mol/h within approximately 1 hour.

The condensation of the product was started with a temperature change of 6° C. between the line upstream and the line downstream of the condenser E1.

As soon as inside the collection vessel V1 the liquid reached the desired level, the condensate obtained from the gas vent (8) was fed to the reactor.

Simultaneously, the feed of azeotropic mixture MeOH/DMC and fresh methanol (7) was started, so as to keep constant the liquid level inside the reactor R1.

After approximately 2 hours, the system had reached steady-state operating conditions, with the flowrate shown in the following, reported in weight units.

The run was continued for about four hours, and 500 g of DMC was produced.

At the end of the test, the composition of the liquid resulted to be substantially the same as of the charged liquid.

TABLE 1

| Stream | 1 | 2 | 3 | 4 | 5 | 6 | 7 | 8 |
|---|---|---|---|---|---|---|---|---|
| $CO_2$ | 26.0 | 1.5 | | 24.5 | | | | |
| CO | 115.0 | 6.5 | | 108.5 | 10.5 | | | |
| $O_2$ | 4.0 | 0.5 | | 3.5 | | 2.5 | | |
| Methanol | 54.0 | 3.0 | 16.0 | 35.0 | | | 25.0 | 3.0 |
| DMC | 12.0 | 0.7 | 5.0 | 6.3 | | | 2.7 | 0.7 |
| $H_2O$ | 8.5 | 0.5 | 3.0 | 5.0 | | | 0.5 | 0.5 |
| Total | 219.5 | 12.7 | 24.0 | 182.8 | 10.5 | 2.4 | 27.2 | 4.2 |

Flowrates reported in g-moles/hour
Condensation: 30%

TABLE 2

| Stream | 1 | 2 | 3 | 4 | 5 | 6 | 7 | 8 |
|---|---|---|---|---|---|---|---|---|
| $CO_2$ | 18.5 | 0.75 | | 17.75 | | | | |
| CO | 74.0 | 3.0 | | 71.00 | 5.25 | | | |
| $O_2$ | 3.5 | 0.15 | | 3.35 | | 1.3 | | |

TABLE 2-continued

| Stream | 1 | 2 | 3 | 4 | 5 | 6 | 7 | 8 |
|---|---|---|---|---|---|---|---|---|
| Methanol | 28.0 | 1.1 | 12.0 | 14.90 | | | 16.1 | 1.1 |
| DMC | 5.5 | 0.2 | 2.7 | 2.60 | | | 1.0 | 0.2 |
| $H_2O$ | 2.5 | 0.1 | 1.5 | 0.90 | | | 0.1 | 0.1 |
| Total | 132.0 | 5.30 | 16.2 | 110.50 | 5.25 | 1.3 | 17.2 | 1.4 |

Flowrates reported in g-moles/hour
Condensation: 50%

TABLE 3

| Stream | 1 | 2 | 3 | 4 | 5 | 6 | 7 | 8 |
|---|---|---|---|---|---|---|---|---|
| $CO_2$ | 9.7 | 0.75 | | 8.95 | | | | |
| CO | 139.0 | 10.75 | | 128.25 | 13.00 | | | |
| $O_2$ | 7.8 | 0.60 | | 7.20 | | 1.7 | | |
| $H_2$ | 42.5 | 3.25 | | 39.25 | 3.25 | | | |
| Methanol | 70.0 | 5.40 | 10.0 | 54.60 | | | 18.4 | 5.4 |
| DMC | 11.0 | 0.80 | 3.0 | 6.20 | | | 2.3 | 0.8 |
| $H_2O$ | 7.0 | 0.50 | 1.5 | 5.00 | | | 0.5 | 0.5 |
| Total | 286.0 | 22.05 | 14.5 | 249.45 | 16.25 | 1.7 | 21.2 | 6.7 |

Flowrates reported in g-moles/hour
Condensation: 20%

What is claimed is:

1. A process for producing dimethyl carbonate by reacting methanol, carbon monoxide, and oxygen in the presence of a cuprous chloride catalyst, the reaction being carried out under pressure and at an elevated temperature in a liquid-gas contact reactor having two parallel, vertical reactor tubes connected with each other at their bottom ends with a bent pipe portion and connected at their top ends to a separating vessel, with one reactor tube being connected to a side of the separating vessel by means of a 90°-bent fitting and with the other reactor tube being connected directly into the separating vessel through a hole in the bottom of the separating vessel; the process consisting essentially of the steps of: (a) charging the reactor tubes with an initial liquid phase consisting essentially of methanol, optionally water, and the suspended catalyst until the liquid phase laps the bottom portion of the 90°-bent fitting then feeding near the bottom of one of the reactor tubes fresh gas consisting essentially of carbon monoxide and oxygen; (c) withdrawing, from the top of the separating vessel, a gas stream which contains gaseous carbon monoxide and oxygen and methanol, dimethyl carbonate, and water vapors; (d) cooling the gas stream to partially condense some of the dimethyl carbonate, methanol and water vapors contained to form a liquid condensate; (e) separating the liquid condensate and recycling the liquid condensate back to the reactor tubes; (f) compressing the cooled gas stream to the pressure of the reactor; and (g) recycling the compressed gas into the bottom of the same reactor tube into which the fresh gas is introduced; (h) adding additional carbon monoxide, oxygen, methanol, and water as needed for the reaction; whereby mixing of the liquid phase in the reactor tubes is accomplished due to the difference in density between the liquid phase in the reactor tube into which the gases are fed and the liquid phase in the other reactor tube; whereby the condensate obtained by partially condensing the vapors in the withdrawn gas stream has a higher concentration of water and dimethyl carbonate than the condensate obtained by totally condensing the vapors in the withdrawn gas stream and whereby the composition of the condensate is similar to the composition of the liquid in the reactor.

2. A process for preparing dimethyl carbonate according to claim 1, wherein the gas stream withdrawn from top of the separating vessel is cooled from 3° to 30° C. to condense from 10 to 70% of the vapors present in the withdrawn gas stream.

3. A process for preparing dimethyl carbonate according to claim 2, wherein the temperature is from 80° C. to 200° C.

4. The process of claim 3, wherein the temperature is 100°–180° C.

5. A process for preparing dimethyl carbonate according to claim 2, wherein the pressure is from 10 to 50 bar.

6. The process according to claim 1, wherein the temperature is from 80° C. to 200° C. and the pressure is from 10 to 50 bar.

7. The process of claim 1, wherein the amount of water in the initial liquid phase is 10–25% by weight.

8. The process of claim 1, wherein the amount of cuprous chloride is 1–20% by weight.

9. The process of claim 1, wherein the feed gas consists essentially of 25–99% carbon monoxide and 1–15% oxygen.

10. The process of claim 1, wherein the amount of cuprous chloride is 1–20% by weight and wherein the feed gas consists essentially of 25–99% carbon monoxide and 1–15% oxygen.

11. The process of claim 10, wherein the feed gas further consists essentially of an inert gas selected from the group consisting of nitrogen, argon, carbon dioxide, and hydrogen.

12. The process of claim 1, wherein the reactor tubes have a diameter of 0.025 to 1 meter and a length of 1.5–20 meters.

13. The process of claim 12, wherein the separating vessel has a diameter 2 to 4 times as large as the diameter of the reactor tubes and a height 2 to 10 times as large as the diameter of the reactor tubes.

14. The process of claim 1, wherein the gas flow rate per each unit of surface area of the cross section of the reactor tube is 100–1000 $m^3/m^2$.

15. The process of claim 1, wherein the amount of water in the initial liquid phase is 10–25% by weight; wherein the amount of cuprous chloride is 1–20% by weight; wherein the feed gas consists essentially of 25–99% carbon monoxide and 1–15% oxygen and the balance, if any, is an inert gas selected from the group consisting of nitrogen, argon, carbon dioxide, and hydrogen; wherein the temperature is from 80° C. to 200° C. and the pressure is from 10 to 50 bar; wherein the amount of dimethyl carbonate in the recycled liquid is 50–60% by weight; wherein the reactor tubes have a diameter of 0.025 to 1 meter and a length of 1.5–20 meters and the separating vessel has a diameter 2 to 4 times as large as the diameter of the reactor tubes and a height 2 to 10 times as large as the diameter of the reactor tubes; wherein the gas flow rate per each unit of surface area of the cross section of the reactor tube is 100–1000 $m^3/m^2$; and wherein the gas stream withdrawn from top of the separating vessel is cooled from 3° to 30° C. to condense from 10 to 70% of the vapors present in the withdrawn gas stream.

16. An improved heterogeneous phase process for producing dimethyl carbonate by reacting methanol, carbon monoxide, and oxygen in the presence of a cuprous chloride catalyst, under pressure and at an elevated temperature in a gas-liquid contact reactor having two parallel, vertical reactor tubes connected with each other at their bottom ends with a bent pipe portion and connected at their top ends to a separating vessel, with one tube being connected to a side of the separating vessel by means of a 90°-bent fitting and with the other tube being connected directly into the separating vessel through a hole in the bottom of the separating vessel; the process being initiated by first feeding a liquid phase containing the solid catalyst and methanol or a methanol-water mixture to a reactor tube in an amount sufficient to lap the 90°-bent fitting; then feeding carbon monoxide and oxygen to the bottom of one of the reactor tubes with mixing of the liquid phase being accomplished due to the density difference between the liquid in the reactor tube to which the gases are fed and the liquid in the other reactor tube; withdrawing, from the top of the separator vessel, a gas stream which contains the gaseous carbon monoxide and oxygen and methanol, water, and dimethyl carbonate vapors; cooling the withdrawn gas stream to condense the methanol, water, and dimethyl carbonate into a liquid condensate; compressing the cooled gases; and recycling the liquid condensate and the compressed gases to the appropriate reactor tubes; the improvement comprising slightly cooling the gas stream withdrawn from the separator so that only a partial liquid condensation of the dimethyl carbonate, methanol, and water vapors occurs, separating the liquid condensate and the gas; compressing the cooled gas to the pressure used in the reaction; recycling the liquid condensate and the compressed gas to the reactor tubes; whereby the condensate obtained by the partial condensation has a higher concentration of water and dimethyl carbonate than the condensate obtained by a total condensation of the vapors in the withdrawn gas stream.

17. A process for preparing dimethyl carbonate according to claim 16, wherein the withdrawn gas stream is cooled from 3° to 30° C. to condense from 10 to 70% of the dimethyl carbonate and water present in the withdrawn gas stream.

18. The process according to claim 16, wherein the temperature is from 80° C. to 200° C. and the pressure is from 10 to 50 bar.

19. The process of claim 16, wherein the reactor tubes have a diameter of 0.025 to 1 meter and a length of 1.5–20 meters and wherein the separating vessel has a diameter 2 to 4 times as large as the diameter of the reactor tubes and a height 2 to 10 times as large as the diameter of the reactor tubes.

20. The process of claim 16, wherein the amount of water in the liquid phase is 10–25% by weight; wherein the amount of cuprous chloride is 1–20% by weight; wherein the feed gas consists essentially of 25–99% carbon monoxide and 1–15% oxygen and the balance, if any, is an inert gas selected from the group consisting of nitrogen, argon, carbon dioxide, and hydrogen; wherein the temperature is from 80° C. to 200° C. and the pressure is from 10 to 50 bar; wherein the reactor tubes have a diameter of 0.025 to 1 meter and a length of 1.5–20 meters and the separating vessel has a diameter 2 to 4 times as large as the diameter of the reactor tubes and a height 2 to 10 times as large as the diameter of the reactor tubes; wherein the gas flow rate per each unit of surface area of the cross section of the reactor tube is 100–1000 $m^3/m^2$; and wherein the gas stream withdrawn from top of the separating vessel is cooled from 3° to 30° C. to condense from 10 to 70% of the vapors present in the withdrawn gas stream.

* * * * *